US00PP37030P2

(12) United States Plant Patent
Lafontaine

(10) Patent No.: US PP37,030 P2
(45) Date of Patent: Oct. 14, 2025

(54) ***HEUCHERA* PLANT NAMED 'FJF 1811'**

(50) Latin Name: *Heuchera hybrida*
Varietal Denomination: FJF 1811

(71) Applicant: Frederic Lafontaine, Bas-Oha (BE)

(72) Inventor: Frederic Lafontaine, Bas-Oha (BE)

( * ) Notice: Subject to any disclaimer, the term of this patent is extended or adjusted under 35 U.S.C. 154(b) by 0 days.

(21) Appl. No.: 18/985,473

(22) Filed: Dec. 18, 2024

(51) Int. Cl.
*A01H 6/80* (2018.01)
*A01H 5/02* (2018.01)

(52) U.S. Cl.
USPC ..... Plt./440

(58) Field of Classification Search
USPC ..... Plt./440
CPC ..... A01H 6/80; A01H 5/02
See application file for complete search history.

*Primary Examiner* — Keith O. Robinson
(74) *Attorney, Agent, or Firm* — Cassandra Bright

(57) ABSTRACT

A new and distinct *Heuchera* cultivar named 'FJF 1811' is disclosed, characterized by fiery red spring and summer foliage with lime-yellow margins and red veins. Flower panicles are bright red with pink. Plants have sturdy, dense habits and strong stems. The new variety is a *Heuchera*, normally produced as an outdoor garden or container plant.

2 Drawing Sheets

Figure 1:
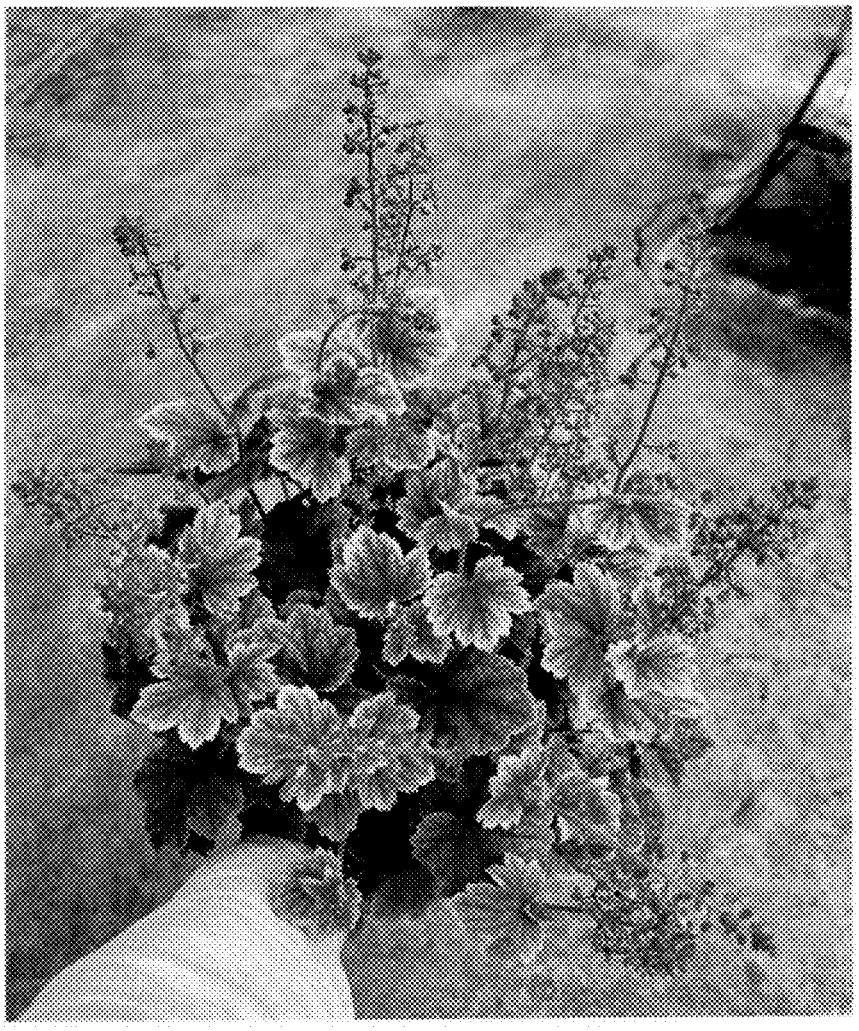

Latin name of the genus and species: *Heuchera hybrida.*
Variety denomination: 'FJF 1811'.

BACKGROUND OF THE INVENTION

The new *Heuchera* cultivar is a product of a planned breeding program conducted by the inventor, in Bas-Oha, Belgium. The objective of the breeding program was to produce new *Heuchera* varieties for ornamental commercial applications. The open-pollination resulting in this new variety was made during 2015.

The seed parent is an unpatented, unnamed variety of *Heuchera americana*. The pollen parent is unidentified. Various species of *Heuchera* were present for pollination. The new variety was selected during 2016 by the inventor in a group of seedlings resulting from the 2015 open-pollination, in a commercial nursery in Bas-Oha, Belgium.

The inventor has filed an application with the CPVO Jul. 1, 2024 having application No. 2024/1509. The first sale of the new variety occurred May 6, 2024 in the Netherlands, indirectly from the inventor. These disclosures fall within the exception allowed under 102 (b) (1).

Asexual reproduction of the new cultivar was performed by division by the inventor in Bas-Oha, Belgium in 2017 and has shown that the unique features of this cultivar are stable and reproduced true to type in successive generations.

SUMMARY OF THE INVENTION

The cultivar 'FJF 1811' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FJF 1811'. These characteristics in combination distinguish 'FJF 1811' as a new and distinct *Heuchera* cultivar:

1. Attractive foliage color. Fiery red in spring and summer with lime-yellow margins and red veins. After summer the foliage turns lime-green with red veins.
2. Flower panicles are bright red with pink.
3. Sturdy, dense habit.
4. Not sensitive to powdery mildew and botrytis.
5. Can be grown in the sun and partial shade.
6. Strong stems.

Plants of the new cultivar 'FJF 1811' are similar to plants of the seed parent, in most horticultural characteristics, however, plants of the new cultivar 'FJF 1811' differ in the following:

1. Foliage of the new cultivar is brighter and more colorful than foliage of the seed parent.
2. Flowers of the new variety are brighter pink than the flowers of the seed parent.

The pollen parent cannot be identified with certainty.

COMMERCIAL COMPARISONS

Plants of the new cultivar 'FJF 1811' are comparable to the variety *Heuchera* 'Shanghai', U.S. Plant Pat. No. 21,859. The two *Heuchera* varieties are similar in most horticultural characteristics; however, the new variety 'FJF 1811' differs in the following:

1. Stems of the new variety are stronger than stems of this comparator.

Plants of the new cultivar 'FJF 1811' are comparable to the variety *Heuchera villosa* 'Tiramisu', U.S. Plant Pat. No. 20,429. The two *Heuchera* varieties are similar in most horticultural characteristics; however, the new variety 'FJF 1811' differs in the following:

1. Stems of the new variety are stronger and shorter than stems of this comparator.
2. Flower color of the new variety is bright red and pink, while the flower color of this comparator is white.
3. Plants of the new variety can be grown in full sun, while plants of this comparator burn in full sun.
4. Plants of the new variety are less sensitive to powdery mildew and botrytis than plants of this comparator.

Plants of the new cultivar 'FJF 1811' are comparable to the variety *Heuchera* 'Happy Flames', U.S. Plant Pat. No. 32,612. The two *Heuchera* varieties are similar in most horticultural characteristics; however, the new variety 'FJF 1811' differs in the following:

1. Leaves of the new variety are larger than leaves of this comparator.
2. Leaf color of the new variety is a stronger and longer-lasting red than the leaf color of this comparator.

BRIEF DESCRIPTION OF THE PHOTOGRAPHS

The accompanying photograph in FIG. 1 illustrates in full color a typical flowering plant of 'FJF 1811' grown outdoors, in a 23 cm pot. Age of the plant photographed is approximately 9 months from a rooted cutting.

Figure 2:
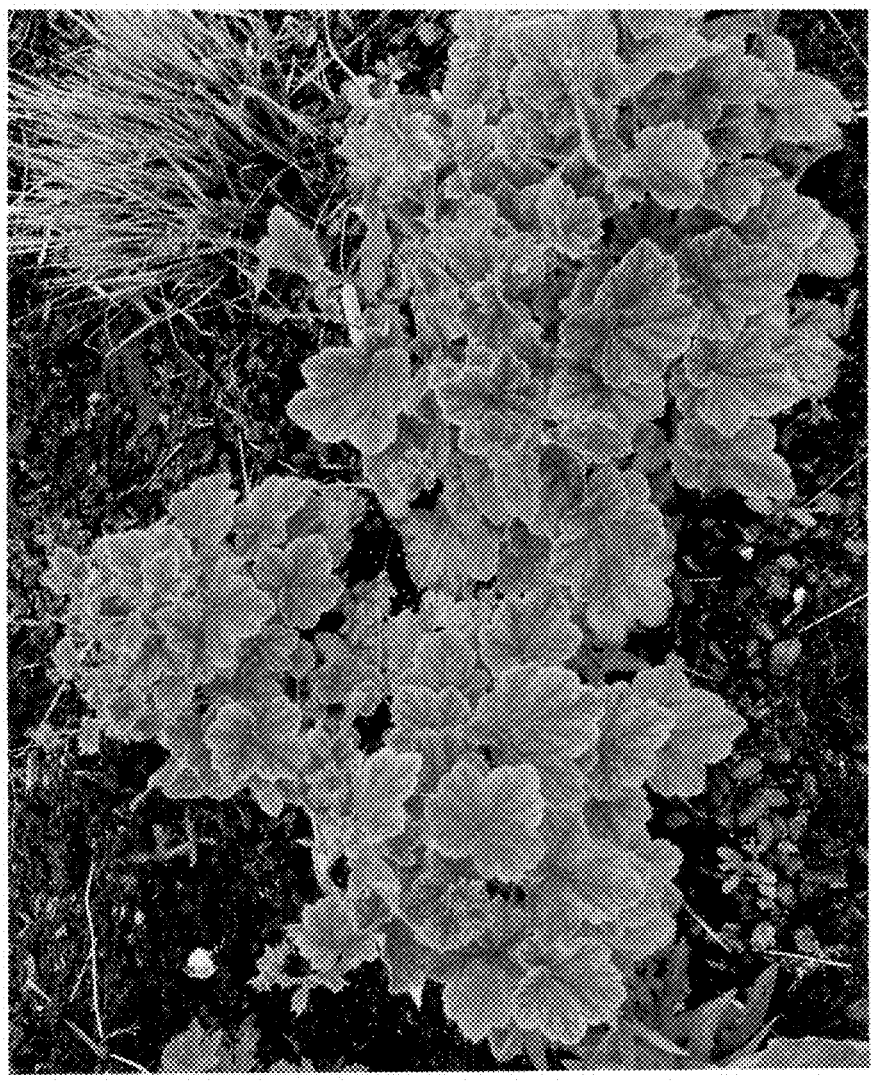

FIG. 2 illustrates 3 plants of the new variety, with Spring foliage at about 7 months old. The photographs were taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society RHS Colour Chart 2015 except where general terms of ordinary dictionary significance are used. The following observations and measurements describe 'FJF 1811' plants grown in a greenhouse, in Bas-Oha, Belgium. The growing temperature ranged from 18° C. to 28° C. during the day and from 13° C. to 18° C. during the night. General light conditions are bright, normal sunlight. Measurements and numerical values represent averages of typical plant types. Plants described were approximately 9 months old.

Botanical classification: *Heuchera hybrida* 'FJF 1811'.

PROPAGATION

Type of propagation typically used: Tissue culture.
Time to Initiate Roots: 8 weeks.
Time from rooted cutting to young plant: 12 weeks to a 15 cm pot.
Root Description: Fibrous, fine.

PLANT

Plant Type: Herbaceous perennial with basal rosettes.
Growth Habit: Mounding, low with upright inflorescences.
Height: 17 cm, excluding inflorescence; 55 cm, including inflorescence.
Plant Spread: 44 cm.
Growth Rate: Vigorous.
Branching Characteristics: No lateral branches, stems emerge from basal rosette.
Number of Rosettes: About 8 to 10.

FOLIAGE

Leaf:
- *Arrangement*.—Rosette, simple.
- *Density of Foliage*.—Medium.
- *Shape of blade*.—Broad ovate to near orbicular. Palmately lobed (5 main lobes per leaf on average).
- *Length*.—Up to 9 cm.
- *Width*.—Up to 9.8 cm.
- *Apex*.—Apiculate.
- *Base*.—Cordate, leaves slightly overlapping.
- *Attachment*.—Petiolate.
- *Margin*.—Crenate.
- *Texture of top surface*.—Pubescent.
- *Texture of bottom surface*.—Pubescent.
- *Glossiness of the leaf blade*.—Young foliage, upper surface: Medium. Young foliage, under surface: Absent Mature foliage, upper surface: Absent to weak Mature foliage under surface: Absent
- *Color*.—Young foliage upper side: RHS Red 185A with 184A; margins Green-Yellow 151C. Young foliage under side: RHS Red 182B to 182C; margins Yellow-Green 150C. Mature foliage upper side: RHS Red 185A with 184A; margins Green-Yellow 151C. Mature foliage under side: RHS Red 182B to 182C; margins Yellow-Green 150C.
- *Venation*.—Type: Palmate. Venation color upper side: RHS Red 185A; midvein Green-Yellow 151C. Venation color under side: RHS Yellow-Green 150C.

Petiole:
- *Length*.—12 cm.
- *Diameter*.—3 mm. Color: RHS Red 59D and Yellow-Green 145C.
- *Texture*.—Glossy.

Stipule:
- *Length*.—1.2 cm.
- *Diameter*.—2 mm.
- *Color*.—Faded RHS Red 59A.

FLOWER

Bloom Period: Summer.

Inflorescence:
- *Type*.—Bell-shaped flowers arranged on panicles.
- *Length*.—54 cm including peduncle; 16 cm excluding peduncle.
- *Diameter*.—5 cm.
- *Quantity*.—5 per plant.
- *Aspect*.—Outward, nodding.
- *Density of flowers in inflorescence*.—Medium.

Bud:
- *Shape*.—Obovate.
- *Length*.—2 mm.
- *Diameter*.—3 mm.
- *Color*.—RHS Red 47A to 47B; base Yellow-Green 145B.
- *Texture*.—Very lightly pubescent.

Individual Flower:
- *Arrangement*.—Single.
- *Shape*.—Campanulate.
- *Quantity*.—Approximately 126 per plant.
- *Length*.—8 mm.
- *Diameter*.—7 mm.
- *Height*.—7 mm.
- *Fragrance*.—None.

Petals:
- *Length*.—3 mm.
- *Width*.—1 mm.
- *Apex*.—Acute.
- *Shape*.—Oblanceolate.
- *Margin*.—Entire.
- *Number*.—5.
- *Base*.—Narrow attenuate.

*Texture*.—Glabrous.

*Color*.—RHS Yellow-Green 148D; base White NN155D.

Sepals:

*Number*.—5.

*Texture*.—Thin, smooth and silky, slightly pubescent.

*Length*.—5 mm.

*Width*.—2 mm.

*Apex*.—Bluntly acute.

*Margin*.—Entire.

Color When opening: RHS Red 47A to 47B. When opened: RHS Yellow-Green 145B.

Calyx:

*Length*.—5 mm.

*Diameter*.—7 mm.

Peduncle:

*Length*.—38 cm.

*Diameter*.—2 mm.

*Angle*.—Upright.

*Strength*.—Moderately strong.

*Texture*.—Pubescent.

*Color*.—RHS Yellow-Green 145C with Red 179A to 179B.

Pedicel:

*Length*.—Primary: 1.3 cm. Secondary: 2 mm.

*Diameter*.—Primary: 1 mm. Secondary: 1 mm.

*Angle*.—75° to 90° from peduncle.

*Strength*.—Moderate.

*Texture*.—Lightly pubescent.

*Color*.—RHS Greyed-Purple 184A.

REPRODUCTIVE ORGANS

Stamens:

*Number*.—5.

*Filament length*.—2 mm.

*Filament width*.—Less than 1 mm.

*Filament color*.—RHS Yellow-Green 150D.

Anthers:

*Length*.—Less than 1 mm.

*Width*.—Less than 1 mm.

*Shape*.—Triangular.

*Color*.—RHS Yellow 4B.

*Pollen*.—Color: RHS Yellow 4B. Quantity: Scant.

Pistil:

*Number*.—2.

*Length*.—About 4 mm.

*Color*.—RHS Yellow-Green 150C.

*Style and Stigma*.—Difficult to distinguish from one another.

*Ovary*.—Length: 3 mm. Width: 2 mm. Color: RHS Yellow-Green 150C.

OTHER CHARACTERISTICS

Fruit/Seed: Not observed.

Disease/pest resistance: Resistance to *Botrytis* and powdery mildew (*Podosphaera macrospora*) has been observed.

Temperature Tolerance: Cold hardy to −25° C.

What is claimed is:

1. A new and distinct cultivar of *Heuchera* plant named 'FJF 1811' as herein illustrated and described.

* * * * *